United States Patent [19]
Brown et al.

[11] Patent Number: 6,010,510
[45] Date of Patent: Jan. 4, 2000

[54] PLUNGER

[75] Inventors: Kyle Brown; Stephen J. Van Noy, both of Fort Worth, Tex.

[73] Assignee: Alcon Laboratories, Inc.

[21] Appl. No.: 09/088,910

[22] Filed: Jun. 2, 1998

[51] Int. Cl.⁷ ..................................................... A61F 9/00
[52] U.S. Cl. ........................................................... 606/107
[58] Field of Search ..................................... 606/107, 166, 606/177

[56] References Cited

U.S. PATENT DOCUMENTS

| | | |
|---|---|---|
| 4,573,998 | 3/1986 | Mazzocco . |
| 4,681,102 | 7/1987 | Bartell . |
| 4,747,404 | 5/1988 | Jampel et al. . |
| 4,834,094 | 5/1989 | Patton et al. . |
| 4,836,201 | 6/1989 | Patton et al. . |
| 4,919,130 | 4/1990 | Stoy et al. . |
| 5,007,913 | 4/1991 | Dulebohn et al. . |
| 5,190,552 | 3/1993 | Kelman . |
| 5,275,604 | 1/1994 | Rheinish et al. . |
| 5,494,484 | 2/1996 | Feingold . |
| 5,499,987 | 3/1996 | Feingold . |
| 5,616,148 | 4/1997 | Eagles et al. . |
| 5,620,450 | 4/1997 | Eagles et al. . |
| 5,653,715 | 8/1997 | Reich et al. . |
| 5,653,753 | 8/1997 | Brady et al. . |
| 5,735,858 | 4/1998 | Makker et al. . |
| 5,800,442 | 9/1998 | Wolf et al. ............................... 606/107 |

Primary Examiner—Michael Buiz
Assistant Examiner—Vy Q. Bui
Attorney, Agent, or Firm—Jeffrey S. Schira

[57] ABSTRACT

An intraocular lens injector plunger having a blunt, rounded tip offset from the centerline of the plunger rod. The offset tip assures that the tip is biased downward against the bottom of the cartridge bore. Such a downward bias helps prevent the tip from riding up over the IOL and being folded within the IOL. The offset also helps prevent the haptics of the IOL from becoming trapped between the plunger rod and the cartridge bore, thereby damaging the haptics and/or preventing the IOL from being advanced down the bore.

2 Claims, 2 Drawing Sheets

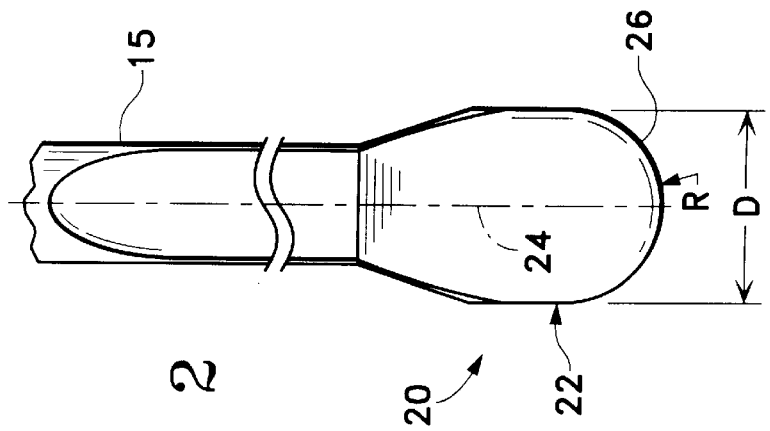
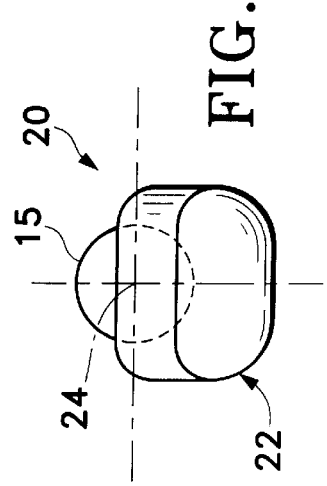
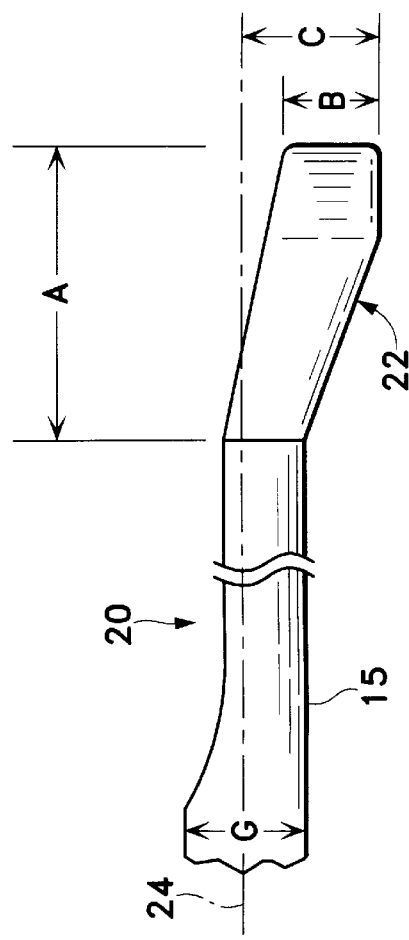

PLUNGER

This invention relates to intraocular lenses (IOLs) and more particularly to cartridges use to inject IOLs into an eye.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. The most commonly used injector cartridge design is illustrated in U.S. Pat. No. 4,681,102 (Bartell), and includes a split, longitudinally hinged cartridge. Similar designs are illustrated in U.S. Pat. Nos. 5,494,484 and 5,499,987 (Feingold) and 5,616,148 and 5,620,450 (Eagles, et al.). In an attempt to avoid the claims of U.S. Pat. No. 4,681,102, several solid cartridges have been investigated, see for example U.S. Pat. No. 5,275,604 (Rheinish, et al.) and 5,653,715 (Reich, et al.).

These prior art devices used plungers that were substantially symmetrical about a longitudinal axis and generally contained a cylindrical or flared soft tip that completely filled the bore of the injector cartridge. See, for example, U.S. Pat. Nos. 4,681,102 (Bartell) and 4,919,130 (Stoy, et al.), and WIPO Publication No. WO 96/29956, the entire contents of which are incorporated herein by reference. Other plungers had hooked or forked tips meant to grasp the edge of the IOL. See for example, U.S. Pat. Nos. 4,573,998 (Mazzocco), 5,494,484 and 5,499,484 (Feingold), 5,616,148 and 5,620,450 (Eagles, et al.) and 5,653,715 (Reich, et al.), the entire contents of which are incorporated herein by reference. One plunger tip recently commercially introduced is designed so that the IOL rolls around the tip as the IOL is advanced down the cartridge. See U.S. Pat. No. 5,735,858 (Makker, et al.), the entire contents of which is incorporated herein by reference.

While these symmetric plunger tip designs work well with robust, rubbery, elastic lens materials, the performance of these tip designs is less than optimal when used with a viscoelastic material, such as a soft acrylic. In particular, the tip design that encourages the IOL to roll around the tip as the tip is advanced down the cartridge bore significantly increases the chances of damage to soft acrylic IOLs. The inventors have also discovered that viscoelastic IOL materials tend to flow around the plunger tip, regardless of tip design, and prior art tips do not address this material property adequately. Accordingly, a need continues to exist for an IOL injector plunger designed to optimize performance when used with a viscoelastic material.

BRIEF SUMMARY OF THE INVENTION

The present invention improves upon prior art lens injector plungers by providing a plunger having blunt, rounded tip offset from the centerline of the plunger rod. The offset tip assures that the tip is biased downward against the bottom of the cartridge bore. Such a downward bias helps prevent the tip from riding up over the IOL and being folded within the IOL, as is illustrated in FIGS. 5 and 6 of U.S. Pat. No. 5,735,858. Folding the IOL about the plunger tip may result in tip advance without advancing the IOL, particularly with viscoelastic materials which tend to be more adherent than elastic or rubber materials. The offset also helps prevent the haptics of the IOL from becoming trapped between the plunger rod and the cartridge bore, thereby damaging the haptics and/or preventing the IOL from being advanced down the bore.

It is accordingly an object of the present invention to provide a lens injector plunger having a rounded tip.

It is a further object of the present invention to provide a lens injector plunger having an offset tip.

It is a further object of the present invention to provide a lens injector plunger that minimizes the potential for damage to the optic and/or the haptics.

Other objects, features and advantages of the present invention will become apparent with reference to the drawings, and the following description of the drawings and claims.

BRIEF DESCRIPTION OF THE DRAWINGS

FIG. 1 is a partial side elevational view of the lens injector plunger of the present invention.

FIG. 2 is a top plan view of the lens injector plunger of the present invention.

FIG. 3 a front elevational view of the lens injector plunger of the present invention.

DETAILED DESCRIPTION OF THE INVENTION

Figure 4:
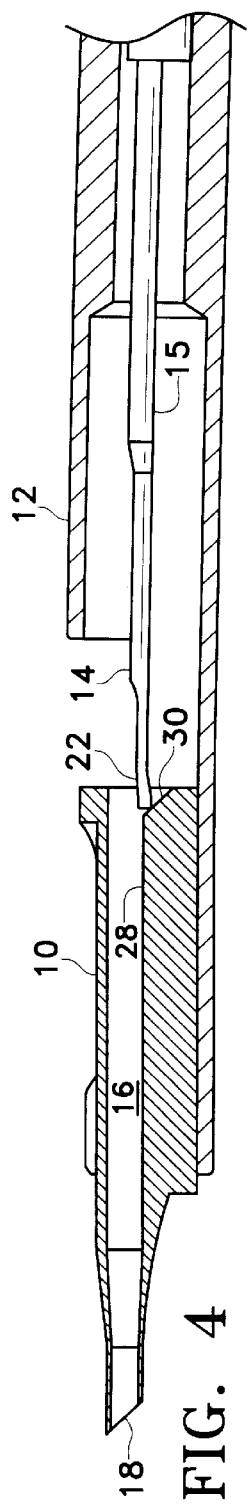
FIGS. 4–4C are partial cross-sectional views of the intraocular lens injector plunger of the present invention traveling down the bore of the lens injector cartridge and handpiece.
Figure 4A:
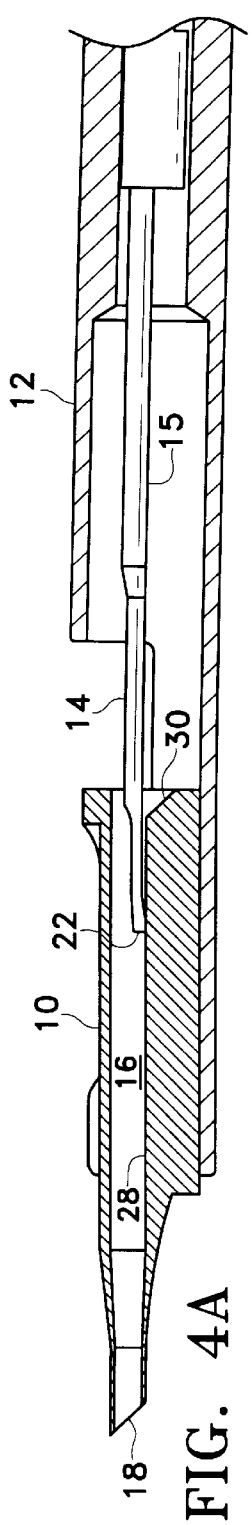
Figure 4B:
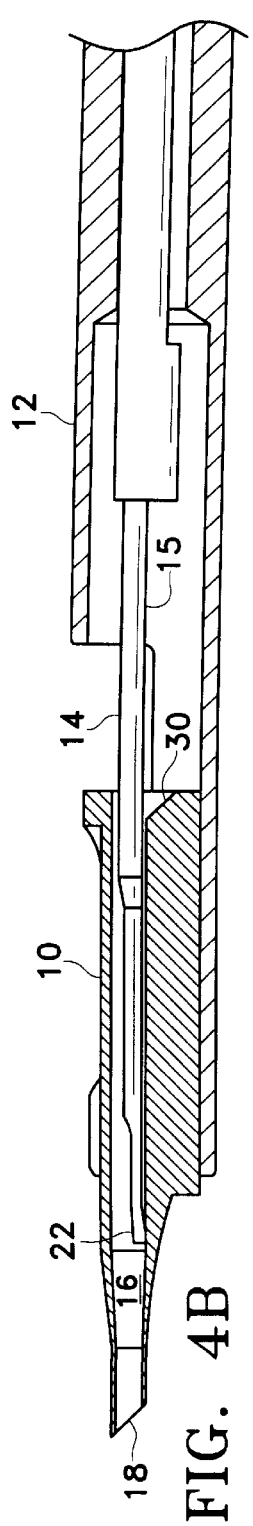

As best seen in FIG. 4, intraocular lens injectors suitable for use with the present invention generally consist of handpiece 10, cartridge 12 and plunger 14. Cartridge 12 contains bore 16 through which the intraocular lens (not shown) is pushed by plunger 14 until the lens exist bore 16 at nozzle 18. Cartridge 10 and handpiece 12 may be of any suitable design well-known in the art.

As best seen in FIGS. 1–3 plunger 14 contains tip 20 that contains IOL contacting portion 22 that is off set asymmetrically relative to longitudinal centerline 24. Portion 22 also contains convexly rounded nose 26. Length A of portion 22 preferably is between 0.10 inches and 0.20 inches, with 0.127 inches being preferred. Width D of portion 22 preferably is between 0.060 inches and 0.100 inches, with 0.083 inches being most preferred. The radius R of nose 26 may be any suitable dimension, with between 0.030 inches and 0.050 inches being preferred and 0.042 inches being most preferred.

The offset distance C from centerline 24 will vary depending upon the diameter of bore 16 and plunger rod 15 and the thickness B of portion 22. By way of example, when bore 16 has a diameter of around 0.100 inches, plunger rod 15 has a diameter G of around 0.060 inches and thickness B of portion 22 is between 0.030 inches and 0.060, offset C generally will be between 0.047 inches and 0.077 inches.

Figure 4C:
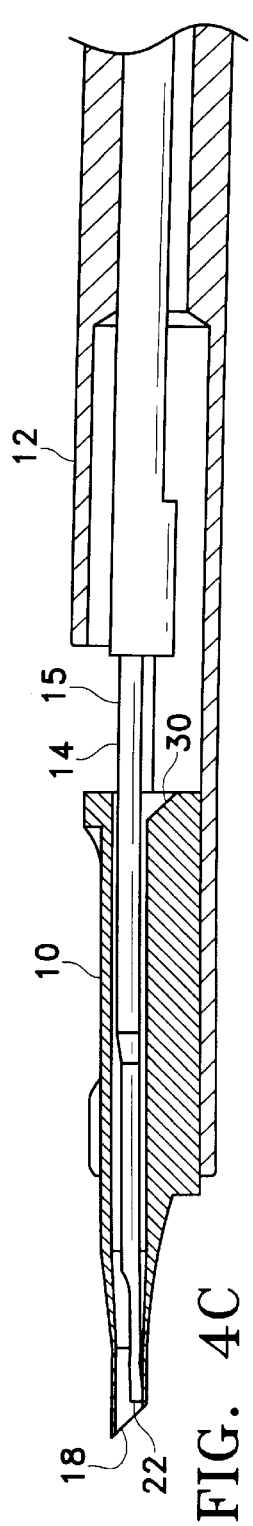

In use, as seen in FIGS. 4–4C, as plunger 14 travels down bore 16, offset portion 22 of tip 20 maintains constant contact with and pressure against bore wall 28, because rod 15 must be deflected slightly in order for tip 20 to enter bore 16. To facilitate the entry of tip 20 into bore 16, cartridge 10 may contain ramped or flared opening 30 so that the initial contact between cartridge 12 and portion 22 occurs on flared portion 30.

While certain embodiments of the present invention have been described above, these descriptions are given for purposes of illustration and explanation. Variations, changes, modifications and departures from the systems and methods disclosed above may be adopted without departure from the scope or spirit of the present invention.

We claim:

1. An intraocular lens injection system, comprising:

a) a handpiece having a plunger, the plunger having a longitudinal centerline;

b) an injection cartridge having a bore, the cartridge to be received in the handpiece so that the plunger can travel down the bore;

c) a tip on the plunger, the tip having a lens contacting portion that is offset asymmetrically relative to the longitudinal centerline so that the tip maintains constant contact with and pressure against a wall of the bore.

2. A plunger for use with an intraocular lens injection system, the system including a handpiece and an injection cartridge having a walled bore, comprising:

a) a plunger rod having a centerline;

b) a tip on the plunger rod, the tip having a lens contacting portion that is offset asymmetrically relative to the centerline so that the tip maintains constant contact with and pressure against the walled bore of the cartridge during use.

* * * * *